(12) United States Patent
Wu et al.

(10) Patent No.: US 10,966,797 B2
(45) Date of Patent: Apr. 6, 2021

(54) IMAGING SYSTEM

(71) Applicant: QISDA CORPORATION, Taoyuan (TW)

(72) Inventors: Tsung-Hsun Wu, Taoyuan (TW); Ming-Kuen Lin, Taoyuan (TW); Hung-Wen Liu, Taoyuan (TW)

(73) Assignee: Qisda Corporation, Taoyuan (TW)

( * ) Notice: Subject to any disclaimer, the term of this patent is extended or adjusted under 35 U.S.C. 154(b) by 0 days.

(21) Appl. No.: 16/830,305

(22) Filed: Mar. 26, 2020

(65) Prior Publication Data
US 2020/0345450 A1 Nov. 5, 2020

(30) Foreign Application Priority Data
Apr. 30, 2019 (CN) .......................... 201910361781.X

(51) Int. Cl.
*A61B 90/00* (2016.01)

(52) U.S. Cl.
CPC .............. *A61B 90/36* (2016.02); *A61B 90/03* (2016.02); *A61B 90/08* (2016.02); *A61B 2090/033* (2016.02); *A61B 2090/0454* (2016.02); *A61B 2090/366* (2016.02); *A61B 2090/3618* (2016.02)

(58) Field of Classification Search
CPC .......... A61B 90/36; A61B 90/03; A61B 90/08
USPC ........................................................ 362/560
See application file for complete search history.

(56) References Cited

U.S. PATENT DOCUMENTS

| | | | |
|---|---|---|---|
| 6,023,289 A * | 2/2000 | Oravecz ................. | A61B 90/36 348/65 |
| 6,785,049 B1 * | 8/2004 | Boyd .................... | G02B 27/283 345/7 |
| 2006/0176242 A1 * | 8/2006 | Jaramaz ................. | A61B 34/20 345/7 |
| 2016/0142683 A1 * | 5/2016 | Seesselberg ......... | G02B 17/008 348/143 |

FOREIGN PATENT DOCUMENTS

CN 109375459 A 2/2019

\* cited by examiner

*Primary Examiner* — Bryon T Gyllstrom

(57) ABSTRACT

An imaging system includes an image generating device and two reflecting mirrors. The image generating device projects a light toward a gravity direction. The two reflecting mirrors are disposed with respect to each other and one of the two reflecting mirrors is disposed with respect to the image generating device. The light projected by the image generating device forms a virtual image through the two reflecting mirrors in sequence.

7 Claims, 5 Drawing Sheets

IMAGING SYSTEM

BACKGROUND OF THE INVENTION

1. Field of the Invention

The invention relates to an imaging system and, more particularly, to an imaging system capable of improving visual effect effectively while watching an image.

2. Description of the Prior Art

A head up display (HUD) is used to project specific information onto a glass by optical reflection principle for a user. Referring to FIG. 1, FIG. 1 is a schematic view illustrating a head up display 1 of the prior art. As shown in FIG. 1, a display device 10 of the head up display 1 projects a light toward an anti-gravity direction D1 (i.e. toward sky) and then the light is reflected by two reflecting mirrors 12, 14 to an eye 2 of a person. When an environmental light source 3 (e.g. lamp, sun, etc.) exists over the head up display 1, the light projected by the display device 10 is influenced by the environmental light source 3 since there is no shelter between the display device 10 and the environmental light source 3. Accordingly, the visual effect is influenced while a user is watching an image generated by the head up display 1. Furthermore, since the display device 10 projects the light toward the anti-gravity direction D1, the eye 2 may watch the display device 10 directly, such that the visual effect is also influenced while the user is watching the image generated by the head up display 1.

SUMMARY OF THE INVENTION

An objective of the invention is to provide an imaging system capable of improving visual effect effectively while watching an image, so as to solve the aforesaid problems.

According to an embodiment of the invention, an imaging system comprises an image generating device and two reflecting mirrors. The image generating device projects a light toward a gravity direction. The two reflecting mirrors are disposed with respect to each other and one of the two reflecting mirrors is disposed with respect to the image generating device. The light projected by the image generating device forms a virtual image through the two reflecting mirrors in sequence.

As mentioned in the above, the image generating device of the invention projects the light toward the gravity direction. When an environmental light source exists over the image generating device, the light projected by the image generating device is not influenced by the light emitted by the environmental light source. Accordingly, the invention can improve the visual effect effectively while a user is watching an image generated by the imaging system of the invention. Furthermore, since the image generating device projects the light toward the gravity direction, the eye of a person does not watch the image generating device directly, such that the visual effect is not influenced while the user is watching the image generated by the imaging system of the invention.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
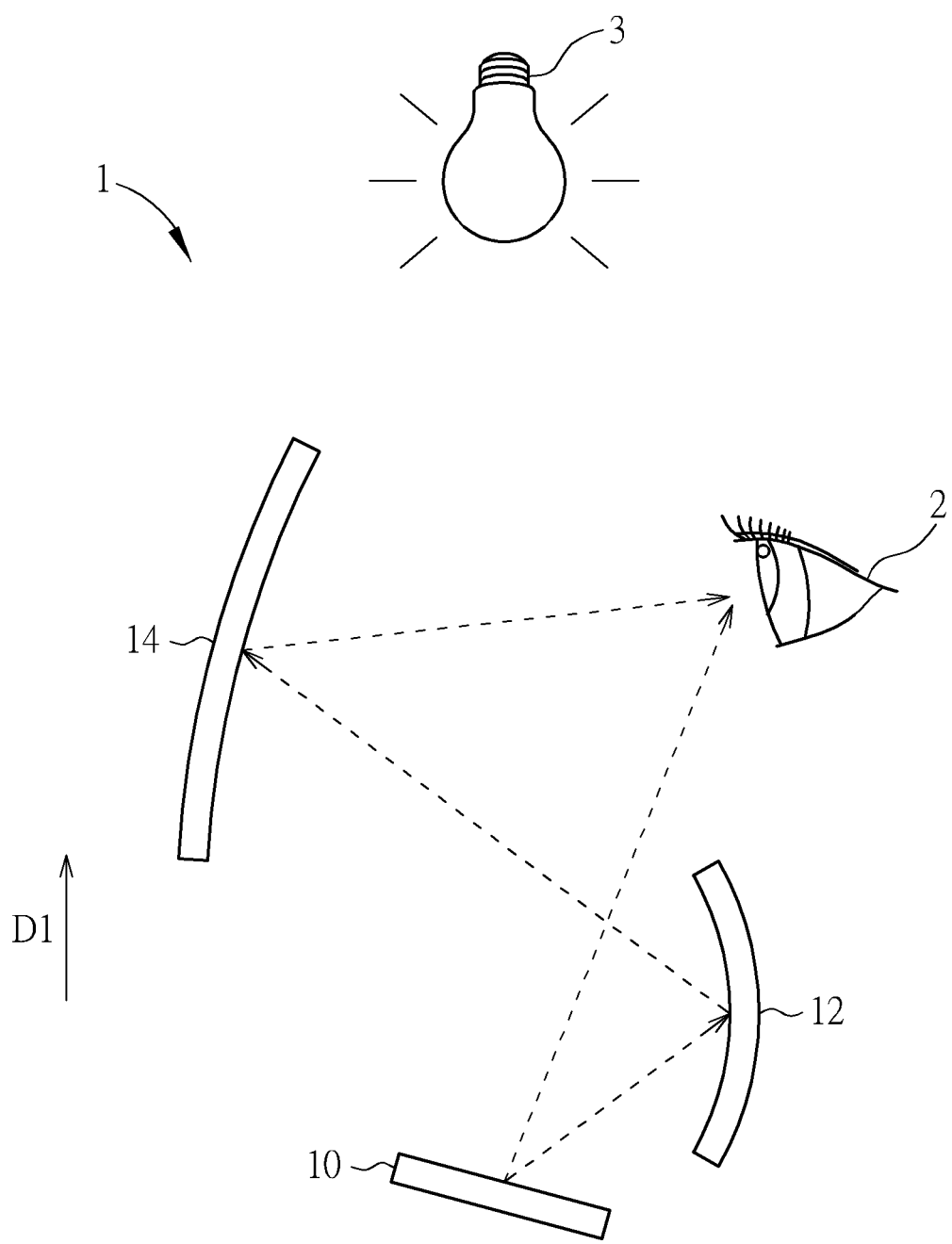
FIG. 1 is a schematic view illustrating a head up display of the prior art.
Figure 2:
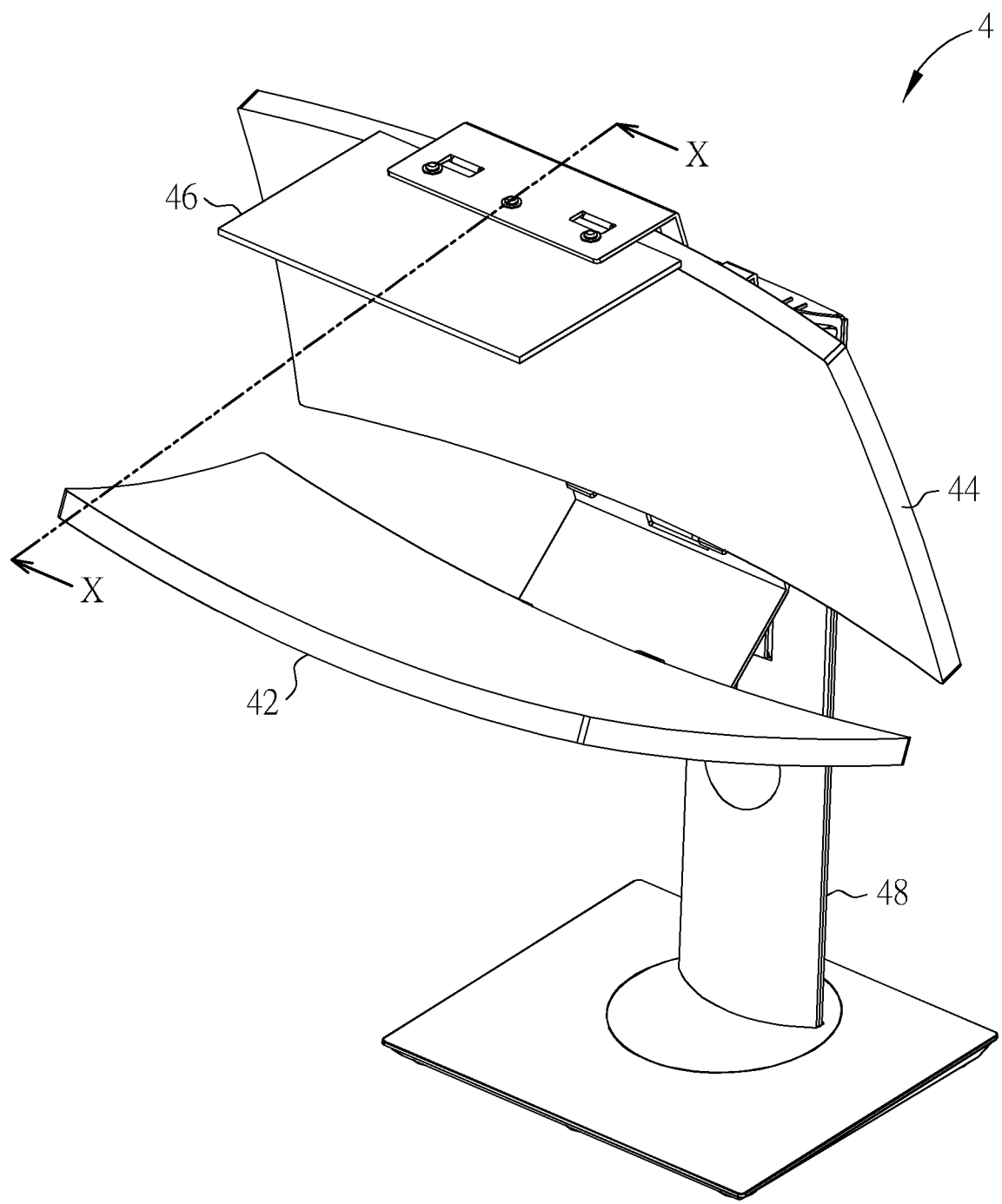
FIG. 2 is a perspective view illustrating an imaging system according to an embodiment of the invention.
Figure 3:
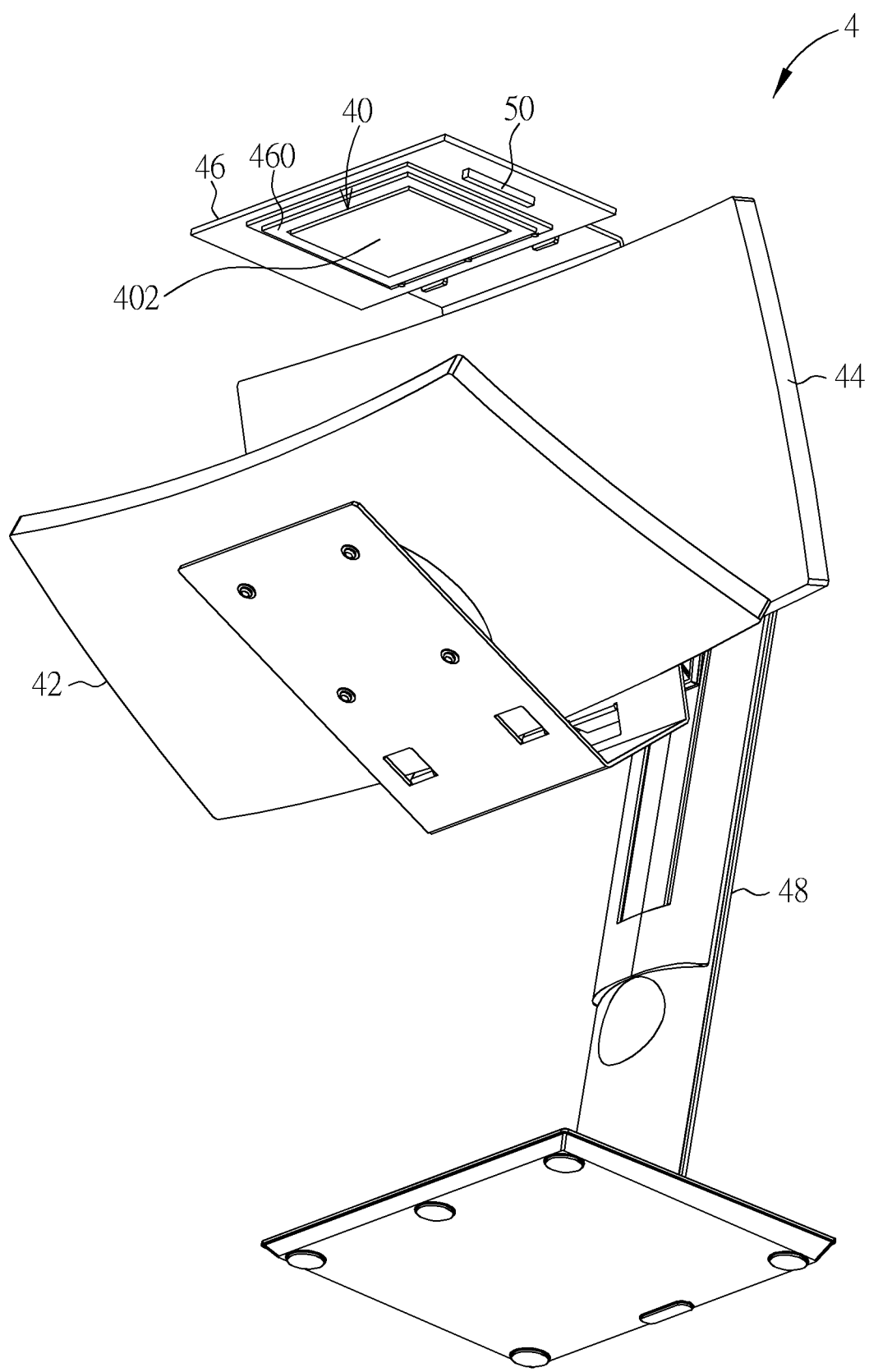
FIG. 3 is a perspective view illustrating the imaging system shown in FIG. 2 from another viewing angle.
Figure 4:
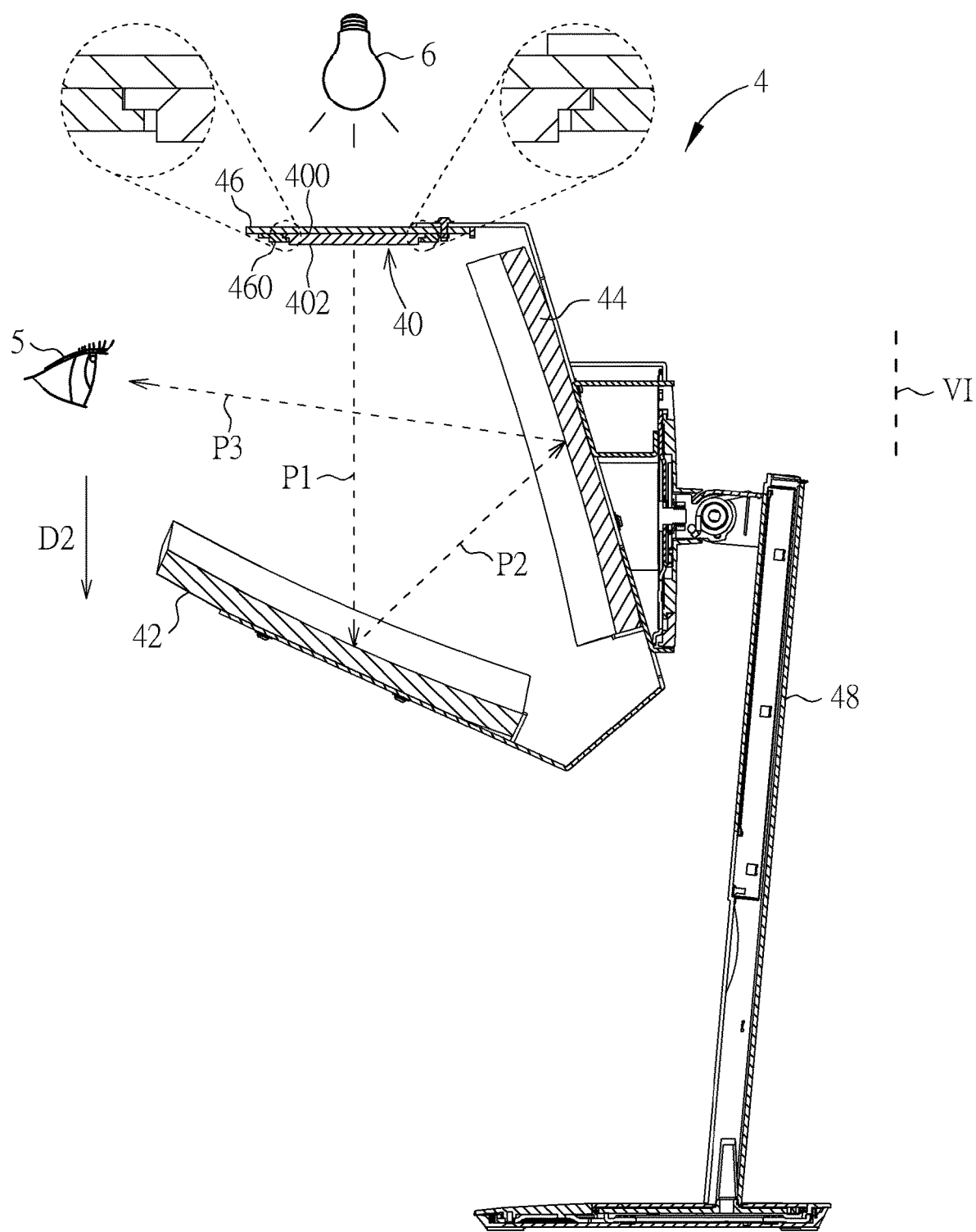
FIG. 4 is a sectional view illustrating the imaging system shown in FIG. 2 along line X-X.

Referring to FIGS. 2 to 4, FIG. 2 is a perspective view illustrating an imaging system 4 according to an embodiment of the invention, FIG. 3 is a perspective view illustrating the imaging system 4 shown in FIG. 2 from another viewing angle, and FIG. 4 is a sectional view illustrating the imaging system 4 shown in FIG. 2 along line X-X.

As shown in FIGS. 2 to 4, the imaging system 4 comprises an image generating device 40, two reflecting mirrors 42, 44, a light shielding base 46, a frame 48 and a light source 50. In this embodiment, the imaging system 4 may be, but not limited to, a head up display or an enlarged display. The image generating device 40 may be a display, a mobile phone or other electronic devices capable of generating images. The two reflecting mirrors 42, 44 may be, but not limited to, concave reflecting mirrors. The light source 50 may be a light emitting diode or other light emitting devices.

The two reflecting mirrors 42, 44 and the light shielding base 46 are disposed on the frame 48, wherein the two reflecting mirrors 42, 44 are disposed with respect to each other. Accordingly, the imaging system 4 may be placed on a plane through the frame 48. The image generating device 40 and the light source 50 are disposed on the light shielding base 46. In this embodiment, the light shielding base 46 may have a positioning structure 460 and the positioning structure 460 positions the image generating device 40 on the light shielding base 46. For example, the positioning structure 460 may be an accommodating recess with retaining wall or elastic sheet, such that a user may engage the image generating device 40 in the positioning structure 460, so as to position the image generating device 40 on the light shielding base 46. Furthermore, the light source 50 may be located around the light shielding base 46.

When the image generating device 40 is disposed on the light shielding base 46, a non-light projection side 400 of the image generating device 40 abuts against the light shielding base 46 and a light projection side 402 of the image generating device 40 is oriented toward a gravity direction D2 (i.e. toward ground). Since the image generating device 40 projects a light from the light projection side 402, the image generating device 40 projects the light toward the gravity direction D2. Furthermore, one of the two reflecting mirrors 42, 44 is disposed with respect to the image generating device 40. In this embodiment, the reflecting mirror 42 is disposed with respect to the image generating device 40, so as to reflect the light projected by the image generating device 40 to the reflecting mirror 44.

As shown in FIG. 4, when the image generating device 40 is powered on, the image generating device 40 projects a light onto the reflecting mirror 42 along a first optical path P1. Then, the first optical path P1 is reflected by the reflecting mirror 42 to form a second optical path P2. Then, the second optical path P2 forms a virtual image VI through the reflecting mirror 44 and the second optical path P2 is reflected by the reflecting mirror 44 to an eye 5 of a person to form a third optical path P3. In other words, the light projected by the image generating device 40 forms the virtual image VI through the two reflecting mirrors 42, 44 in sequence.

As shown in FIG. 4, when an environmental light source 6 (e.g. lamp, sun etc.) exists over the image system 4, the light projected by the image generating device 40 is not influenced by the light emitted by the environmental light source 6 since the image generating device 40 projects the light toward the gravity direction D2. Accordingly, the invention can improve the visual effect effectively while a user is watching the image generated by the imaging system 4 of the invention. Furthermore, since the image generating device 40 projects the light toward the gravity direction D2, the eye 5 does not watch the image generating device 40 directly, such that the visual effect is not influenced while the user is watching the image generated by the imaging system 4 of the invention. Still further, the light shielding base 46 can shield stray light generated by the environmental light source 6 effectively, such that the invention can further prevent the stray light from influencing the image. Moreover, when the brightness of the image is insufficient, the user may control the light source 50 to supply light, so as to enhance the visual effect of the image.

Figure 5:
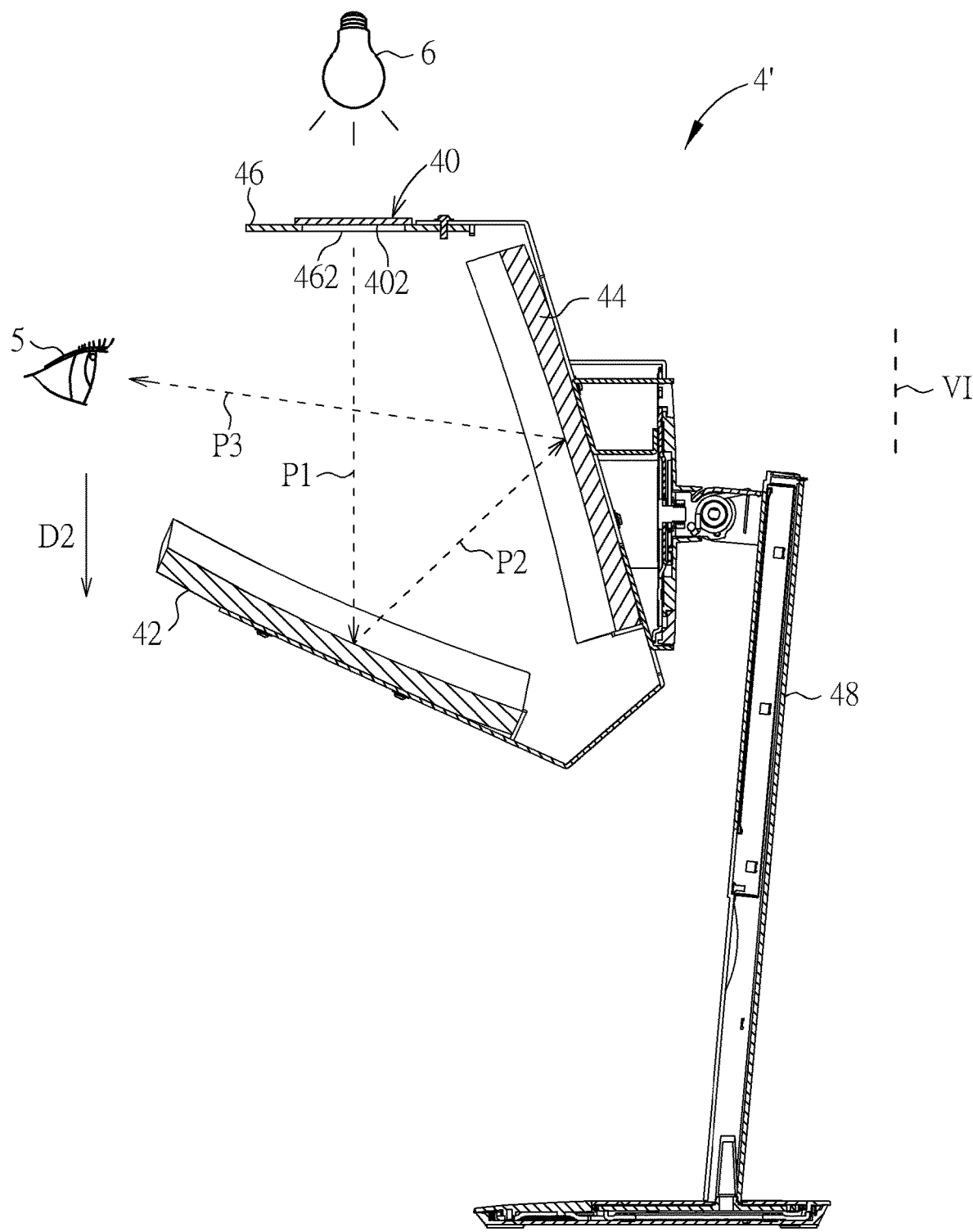
FIG. 5 is a schematic view illustrating an imaging system according to another embodiment of the invention.

Referring to FIG. 5, FIG. 5 is a schematic view illustrating an imaging system 4' according to another embodiment of the invention. The main difference between the imaging system 4' and the aforesaid imaging system 4 is that the light projection side 402 of the image generating device 40 of the imaging system. 4' abuts against the light shielding base 46 and the light shielding base 46 has a light transmissive region 462, such that the image generating device 40 projects the light through the light transmissive region 462, as shown in FIG. 5. In other words, the user may place the light projection side 402 of the image generating device 40 on the light shielding base 46 directly, such that the image generating device 40 projects the light through the light transmissive region 462 toward the gravity direction D2. Accordingly, the light shielding base 46 may remove the aforesaid positioning structure 460. In this embodiment, the light transmissive region 462 may be a hole or made of a light transmissive material according to practical applications.

As mentioned in the above, the image generating device of the invention projects the light toward the gravity direction. When an environmental light source exists over the image generating device, the light projected by the image generating device is not influenced by the light emitted by the environmental light source. Accordingly, the invention can improve the visual effect effectively while a user is watching an image generated by the imaging system of the invention. Furthermore, since the image generating device projects the light toward the gravity direction, the eye of a person does not watch the image generating device directly, such that the visual effect is not influenced while the user is watching the image generated by the imaging system of the invention. Still further, the light shielding base can shield stray light generated by the environmental light source effectively, such that the invention can further prevent the stray light from influencing the image. Moreover, when the brightness of the image is insufficient, the user may control the light source to supply light, so as to enhance the visual effect of the image.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An imaging system comprising:
   an image generating device projecting a light toward a gravity direction; and
   two reflecting mirrors disposed with respect to each other, one of the two reflecting mirrors being disposed under the image generating device and tilted relative to the gravity direction, the other one of the two reflecting mirrors being disposed next to the image generating device and the one of the two reflecting mirrors and located between the image generating device and the one of the two reflecting mirrors, the light projected by the image generating device forming a virtual image by being incident to the one of the two reflecting mirrors along the gravity direction and reflected toward the other one of the two reflecting mirrors in sequence.

2. The imaging system of claim 1, further comprising a light shielding base, the image generating device being disposed on the light shielding base.

3. The imaging system of claim 2, wherein a non-light projection side of the image generating device abuts against the light shielding base.

4. The imaging system of claim 2, wherein a light projection side of the image generating device abuts against the light shielding base and the light shielding base has a light transmissive region, such that the image generating device projects the light through the light transmissive region.

5. The imaging system of claim 2, wherein the light shielding base has a positioning structure and the positioning structure positions the image generating device on the light shielding base.

6. The imaging system of claim 2, further comprising a frame, the two reflecting mirrors and the light shielding base being disposed on the frame.

7. The imaging system of claim 2, further comprising a light source disposed on the light shielding base.

* * * * *